(12) United States Patent
Cheng et al.

(10) Patent No.: US 8,974,920 B2
(45) Date of Patent: Mar. 10, 2015

(54) APPLICATION OF TRIPHENYLENE DERIVATIVES IN ORGANIC ELECTROLUMINESCENT DEVICES

(75) Inventors: Chien-Hong Cheng, Hsinchu (TW); Yu-Han Chen, Hsinchu (TW); Ho-Hsiu Chou, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 661 days.

(21) Appl. No.: 13/238,469

(22) Filed: Sep. 21, 2011

(65) Prior Publication Data
US 2013/0001521 A1 Jan. 3, 2013

(30) Foreign Application Priority Data

Jun. 28, 2011 (TW) .............................. 100122581 A

(51) Int. Cl.
| | |
|---|---|
| H01L 51/54 | (2006.01) |
| C09K 11/06 | (2006.01) |
| C07C 13/66 | (2006.01) |
| C07D 209/86 | (2006.01) |
| C07C 211/54 | (2006.01) |
| C07C 211/58 | (2006.01) |
| C07C 15/62 | (2006.01) |
| H05B 33/14 | (2006.01) |
| H01L 51/00 | (2006.01) |
| H01L 51/50 | (2006.01) |

(52) U.S. Cl.
CPC ............ *C07D 209/86* (2013.01); *C07C 211/54* (2013.01); *C07C 211/58* (2013.01); *C07C 15/62* (2013.01); *C09K 11/06* (2013.01); *H05B 33/14* (2013.01); *H01L 51/0054* (2013.01); *H01L 51/006* (2013.01); *H01L 51/0059* (2013.01); *H01L 51/0072* (2013.01); *H01L 51/5012* (2013.01); *C07C 2103/42* (2013.01); *C09K 2211/1007* (2013.01); *C09K 2211/1011* (2013.01); *C09K 2211/1029* (2013.01); *Y10S 428/917* (2013.01)
USPC ............. 428/690; 428/917; 313/504; 257/40; 257/E51.024; 548/445; 585/26

(58) Field of Classification Search
None
See application file for complete search history.

(56) References Cited

U.S. PATENT DOCUMENTS

| | | | | |
|---|---|---|---|---|
| 2006/0246317 | A1* | 11/2006 | Lyu et al. | 428/690 |
| 2007/0100180 | A1* | 5/2007 | Egawa et al. | 585/26 |
| 2010/0140604 | A1* | 6/2010 | Yamada et al. | 257/40 |
| 2011/0254436 | A1* | 10/2011 | Cheng et al. | 313/504 |

FOREIGN PATENT DOCUMENTS

| | | | |
|---|---|---|---|
| JP | 2011157359 A | * | 8/2011 |
| WO | WO 2011132624 A1 | * | 10/2011 |

OTHER PUBLICATIONS

Machine translation of JP 2011-157359. Date of publication: Aug. 18, 2011.*

* cited by examiner

*Primary Examiner* — Andrew K Bohaty
(74) *Attorney, Agent, or Firm* — Rosenberg, Klein & Lee

(57) ABSTRACT

Triphenylene derivatives having a structure of formula (1) are provided. Ar represents an aromatic compound, n is 1 to 3, and each of R and $R_1$ to $R_{13}$ is a member independently selected from the group consisting of hydrogen, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl. The compound of the present invention may function as a host emitter or dopant in the emitter layer of OLED device. An OLED device is also herein provided.

7 Claims, 1 Drawing Sheet

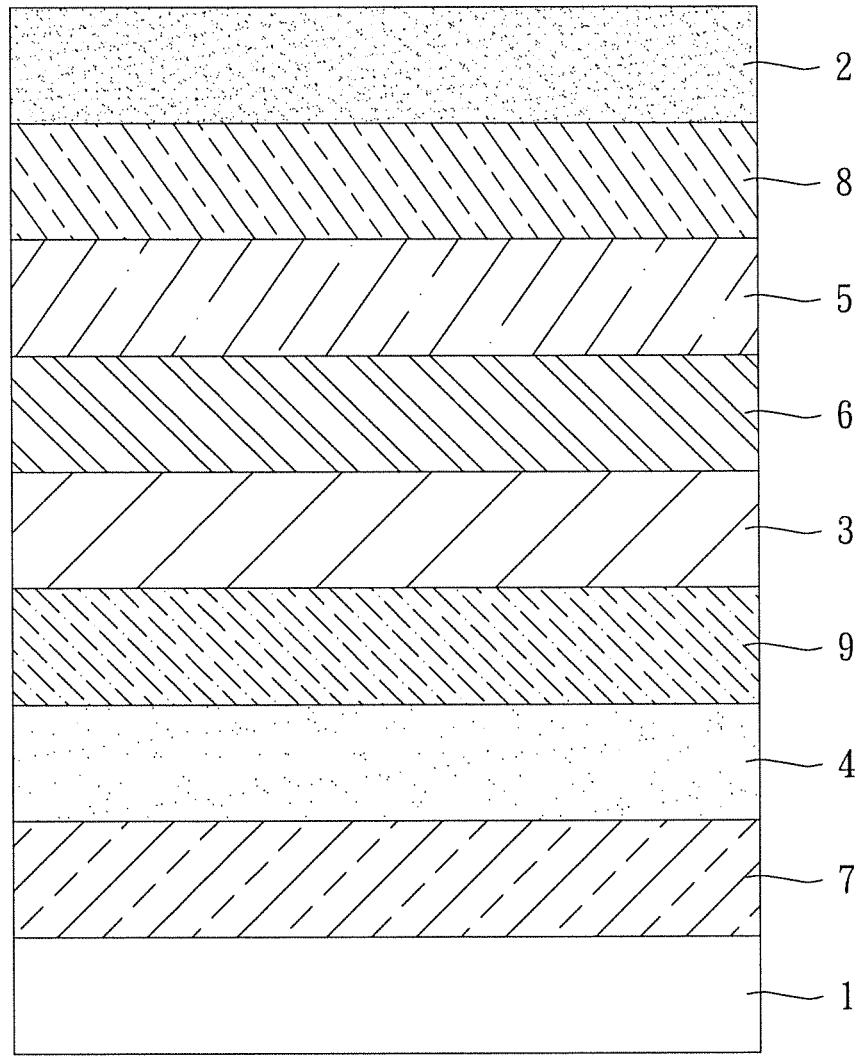

APPLICATION OF TRIPHENYLENE DERIVATIVES IN ORGANIC ELECTROLUMINESCENT DEVICES

BACKGROUND OF THE INVENTION

1. Field of the Invention

The present invention relates to a novel compound and organic light emitting diode using the same, particularly to triphenylene derivatives and organic light emitting diode using the same.

2. Description of the Prior Art

Organic light emitting diode (OLED) has been a great topic of interest for many researchers due to its advantageous application in flat panel displays. The development of stable and highly efficient three primary color (red, green and blue) emitting materials and devices is crucial for OLEDs to become commercial products. One important requirement in the development of organic electroluminescent devices is to develop RGB (red, green, and blue) light emitting devices so as to satisfy the need of a color flat panel display.

The hunt for efficient blue electroluminescence is of particular interest because it is an essential component to realize OLEDs in display as well as lighting applications. Many research groups have successfully prepared efficient blue fluorophores and their OLEDs. However, at the present time, the efficient ones with good Commission Internationale d'Énclairage y coordinate value $(CIE_y) \leq 0.15$ are still relatively rare. At the present time, there is a lack of good organic electroluminescence compounds that will satisfy the aforementioned need.

To sum up, it is highly desirable to develop new organic compounds that can be advantageously used in the low power consumption organic electroluminescent devices which can emit luminescence especially in blue color spectrum.

SUMMARY OF THE INVENTION

The present invention is directed to triphenylene derivatives and organic light emitting diode using the same.

According to one embodiment, a triphenylene derivative has a structure of formula (1), wherein Ar represents an aromatic compound, n is 1 to 3, and each of R and $R_1$ to $R_{13}$ is a member independently selected from the group consisting of hydrogen, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

According to another embodiment, an organic light emitting diode includes a cathode, an anode and an emitting layer. The emitting layer is configured between the cathode and the anode and includes the aforementioned triphenylene derivative.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein:

The FIGURE is a schematic diagram illustrating OLED configuration containing triphenylene derivatives of the present invention.

DESCRIPTION OF THE PREFERRED EMBODIMENT

Triphenylene derivatives of the present invention having a structure of formula (1) are provided:

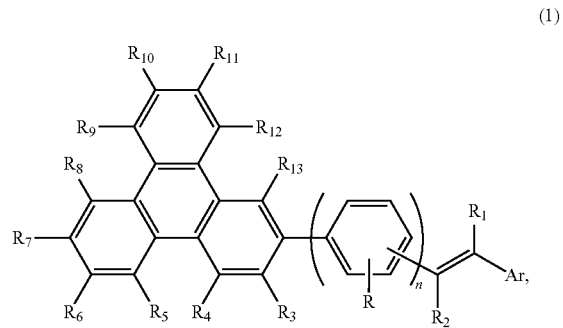

(1)

wherein Ar represents an aromatic compound, n is 1 to 3, and each of R and $R_1$ to $R_{13}$ is a member independently selected from the group consisting of hydrogen, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

In one preferred embodiment, the triphenylene derivatives of the present invention have structures of formulae (1-1) and (1-2).

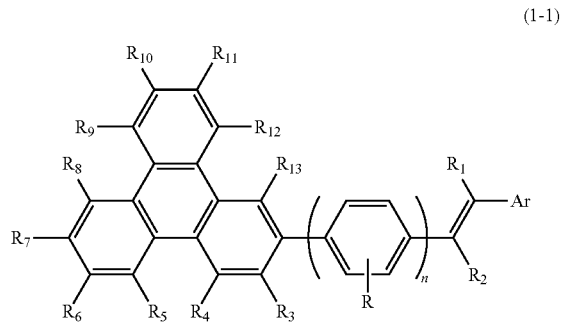

(1-1)

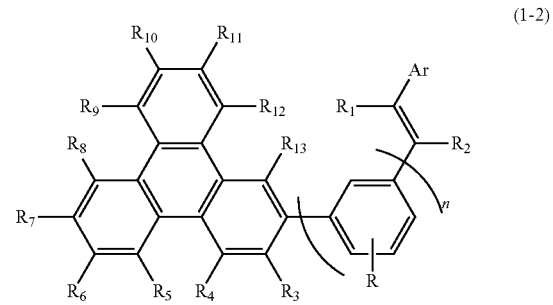

(1-2)

In another preferred embodiment, the triphenylene derivatives of the present invention have structures of formulae (2), (2-1) and (2-2).

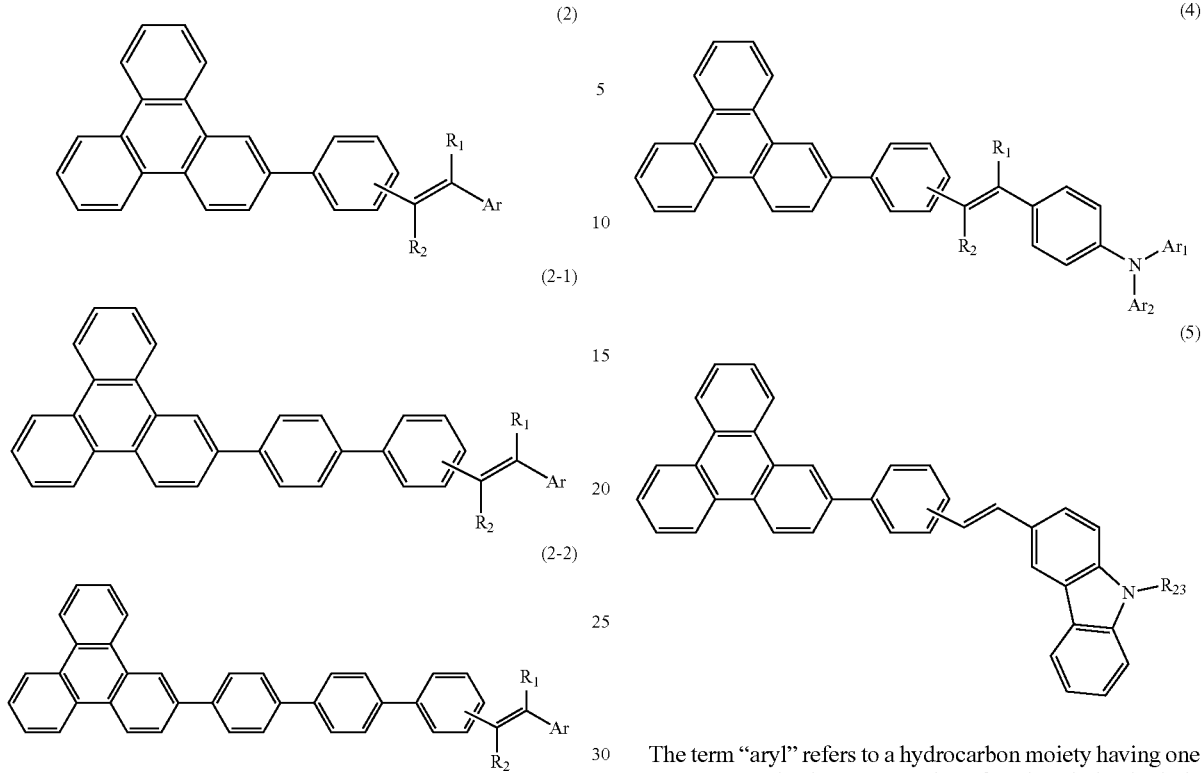

Preferably, the Ar substituent of the present invention is phenyl, and the triphenylene derivatives may be represented by formula (3).

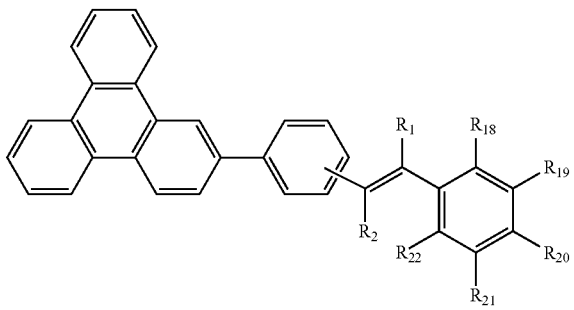

Each of $R_{18}$ to $R_{22}$ is a member independently selected from the group consisting of hydrogen, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

In another embodiment, the Ar substituent in formula (2) may be a phenyl group provided with a substituent containing nitrogen, and provided examples may include formulae (4) or (5), where $Ar_1$ and $Ar_2$ are aromatic compounds and $R_{23}$ in formula (5) is a member selected from the group consisting of hydrogen, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

The term "aryl" refers to a hydrocarbon moiety having one or more aromatic rings. Examples of aryl moieties include phenyl (Ph), phenylene, naphthyl, naphthylene, pyrenyl, anthryl, phenanthryl and triphenylenyl.

The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl and heteroaryl mentioned herein include both substituted and unsubstituted moieties, unless specified otherwise.

Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

Compound Synthesis

The preparation steps and luminescence properties of triphenylene derivatives of the present invention are now detailed as following.

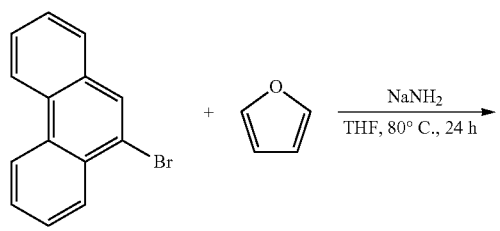

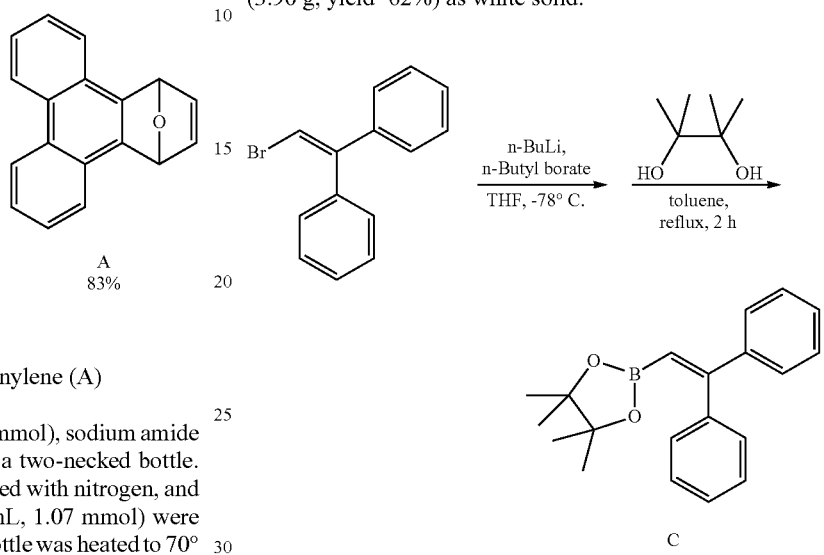

1,4-Dihydro-1,4-epoxytriphenylene (A)

9-Bromophenanthrene (18.6 g, 72.3 mmol), sodium amide (8.47 g, 217.0 mmol) were charged in a two-necked bottle. The bottle was then vacuumed and purged with nitrogen, and dried THF (120 mL) and furan (78.1 mL, 1.07 mmol) were added to the bottle. The mixture in the bottle was heated to 70° C. for reaction for 24 hours, and the resulting was filtered to remove metal. The filtrate was condensed to remove the solvent, and then purified by chromatography with hexanes to yield A (14.7 g, 83%) as white solid powder.

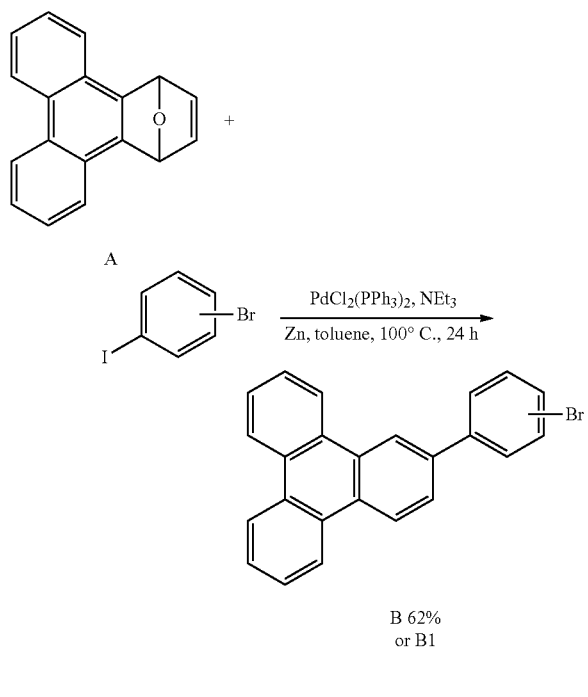

2-(4-Bromophenyl)triphenylene (B)

Compound A (4.0 g, 16.4 mmol), zinc (10.72 g, 163.9 mmol), PdCl$_2$(PPh$_3$)$_2$ (1.16 g, 1.7 mmol), and 1-bromo-4-iodobenzene (4.64 g, 16.4 mmol) or 1-bromo-3-iodobenzene were charged in a two-necked bottle. The bottle was then vacuumed and purged with nitrogen, and dried toluene (100 mL) and triethyl amine (23.0 mL, 165.9 mmol) were added to the bottle. The mixture in the bottle was heated to 110° C. for reaction for 24 hours, and the resulting was filtered to remove metal. The filtrate was condensed to remove the solvent, and then purified by chromatography with hexanes to obtain B (3.90 g, yield=62%) as white solid.

2-(2,2-Diphenylvinyl)-4,4,5,5-tetramethyl-1,3,2-dioxaborolane (C)

n-Butyllithium in hexane (2.5 M, 20 mL) was added slowly under nitrogen to a stirred solution of 2,2-diphenylvinyl bromide (6.50 g, 25.1 mmol) in THF (40 mL) at −78° C. and then the mixture was stirred further for 1 h. n-Butyl borate (15 mL, 55.5 mmol) was added at −78° C. before the mixture was warmed slowly to room temperature and stirred overnight. Water (50 mL) was added, followed by conc. HCl (100 mL) to acidify the mixture, which was then stirred for 3 h. The reaction mixture was extracted with EtOAc and the combined organic phases were dried over MgSO$_4$. Concentration under reduced pressure gave 2,2-diphenylvinyl boronic acid, which, without further purification, was reacted with pinacol (4.25 g, 36.0 mmol) in toluene under reflux for 2 h to effect condensation by the azeotropic removal of the water formed. The mixture was concentrated under reduced pressure and the residue was purified by column chromatography (hexanes/CH$_2$Cl$_2$=1/1) to afford C (4.10 g, 53%) as transparent liquid.

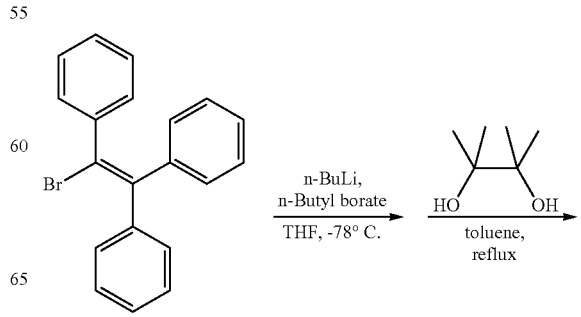

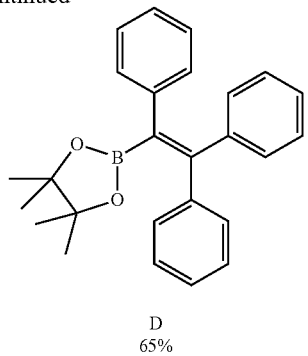

D
65%

4,4,5,5-Tetramethyl-2-(1,2,2-triphenylvinyl)-1,3,2-dioxaborolane (D)

n-Butyllithium in hexane (2.5 M, 15 mL) was added slowly under nitrogen to a stirred solution of (2-bromoethene-1,1,2-triyl)tribenzene (5.00 g, 14.9 mmol) in THF (50 mL) at −78° C. and then the mixture was stirred further for 1 h. Tributyl borate (11.0 mL, 40.8 mmol) was added at −78° C. before the mixture was warmed slowly to room temperature and stirred for 8 hours. Water (100 mL) was added, followed by conc. HCl (100 mL) to acidify the mixture, which was then stirred for 2 hours. The reaction mixture was extracted with EtOAc and the combined organic phases were dried over $MgSO_4$. Concentration under reduced pressure gave 1,2,2-triphenylvinylboronic acid, which, without further purification, was reacted with pinacol (1.73 g, 14.6 mmol) in toluene under reflux for 2 hours to effect condensation by the azeotropic removal of the water formed. The mixture was concentrated under reduced pressure and the residue was purified by column chromatography (hexanes/EtOAc=20/1) to afford D (2.41 g, 65%) as white solid.

(E)-2-(4-Styrylphenyl)triphenylene (TSP)

The product B (400 mg, 1.04 mmol) or B1, (E)-styrylboronic acid (185 mg, 1.25 mmol), potassium carbonate solution (2.0 M, 4.0 mL) and dried toluene (12 mL) were charged in a two-necked bottle. The bottle was deoxygenated and purged with nitrogen, and the mixture in the bottle was stirred at 60° C. until it was totally dissolved. The nitrogen pressure of the bottle was increased, and $Pd(PPh_3)_4$ (120 mg, 0.1 mmol) was rapidly added into the bottle. The reaction was heated to 110° C., and stirred for 48 hours. The resulting was cooled to room temperature to precipitate a solid, and the solid was collected by filtering. The solid was washed by water and methanol, and then sublimated at a temperature of 230° C. to obtain TSP (317 mg, yield=75%) as white solid.

$^1$H NMR (400 MHz, $CDCl_3$): δ 8.87 (d, J=1.6 Hz, 1H), 8.77-8.65 (m, 5H), 7.92 (dd, J=8.6, J=1.6 Hz, 1H), 7.80 (d, J=8.4 Hz, 2H), 7.69-7.66 (m, 6H), 7.56 (d, J=8.0 Hz, 2H), 7.38 (t, J=7.6 Hz, 2H), 7.28 (d, J=7.2 Hz, 1H), 7.20 (s, 2H).

$^{13}$C NMR (100 MHz, $CDCl_3$): δ 140.3, 139.3, 137.3, 136.7, 130.2, 130.1, 129.8, 129.6, 129.0, 129.0, 128.7, 128.2, 127.7, 127.6, 127.4, 127.3, 127.3, 127.1, 126.6, 126.1, 124.0, 123.4. 123.4, 121.5.

HRMS (m/z): [M$^+$] calcd. for $C_{32}H_{22}$, 406.1722. Found, 406.1723.

Anal. calcd for $C_{32}H_{22}$: C, 94.55; H, 5.45. Found: C, 94.42; H, 5.50.

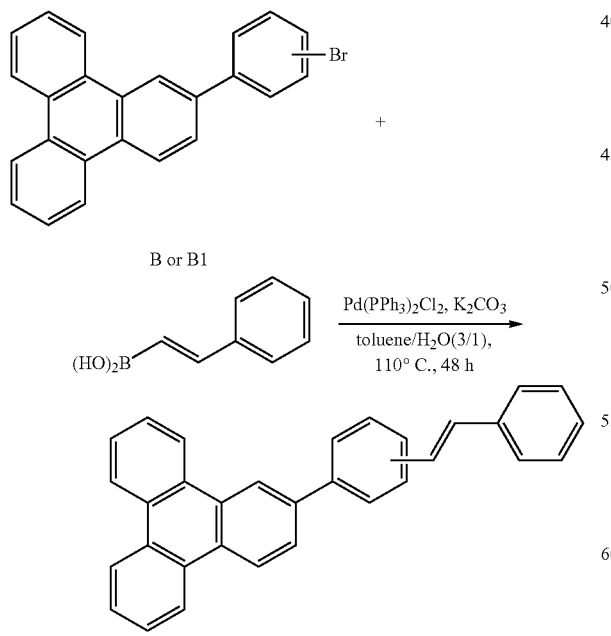

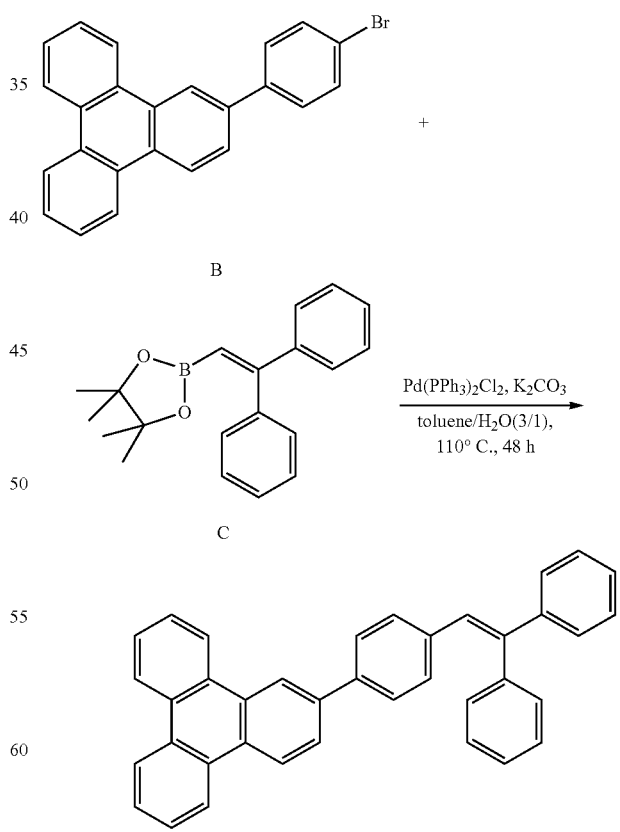

2-(4-(2,2-Diphenylvinyl)phenyl)triphenylene (TSDP)

The product B (451 mg, 1.18 mmol), C (435 mg, 1.42 mmol), potassium carbonate solution (2.0 M, 8.0 mL), and dried toluene (24 mL) were charged in a two-necked bottle. The bottle was deoxygenated and purged with nitrogen, and the mixture in the bottle was stirred at 60° C. until it was totally dissolved. The nitrogen pressure of the bottle was increased, and Pd(PPh$_3$)$_4$ (139 mg, 0.12 mmol) was rapidly added into the bottle. The reaction was heated to 110° C., and stirred for 48 hours. The resulting was cooled to room temperature to precipitate a solid, and the solid was collected by filtering. The solid was washed by water and methanol, and then sublimated at a temperature of 250° C. to obtain TSDP (388 mg, yield=68%) as white solid.

$^1$H NMR (400 MHz, CDCl$_3$): δ 8.80 (d, J=1.6 Hz, 1H), 8.71-8.63 (m, 5H), 7.85 (dd, J=8.4, J=1.6 Hz, 1H), 7.67-7.64 (m, 4H), 7.60 (d, J=8.4 Hz, 2H), 7.39-7.27 (m, 10H), 7.17 (d, J=8.4 Hz, 2H), 7.04 (s, 1H).

$^{13}$C NMR (100 MHz, CDCl$_3$): δ 143.4, 142.9, 140.5, 139.2, 139.2, 136.8, 130.4, 130.2, 130.1, 130.1, 129.8, 129.8, 129.6, 128.9, 128.8, 128.3, 127.7, 127.6, 127.6, 127.6, 127.3, 127.3, 127.2. 126.8, 126.0, 123.9, 123.4, 123.3, 121.4.

HRMS (m/z): [M$^+$] calcd. for C$_{38}$H$_{26}$, 482.2035. Found, 482.2036.

Anal. calcd for C$_{38}$H$_{26}$: C, 94.57; H, 5.43. Found: C, 94.35; H, 5.33.

2-(4-(1,2,2-Triphenylvinyl)phenyl)triphenylene (TSTP)

The product B (1.25 g, 3.26 mmol), D (1.37 g, 3.58 mmol), potassium carbonate solution (K$_2$CO$_3$(aq), 2.0 M, 8.0 mL), and dried toluene (24 mL) were charged in a two-necked bottle. The bottle was deoxygenated and purged with nitrogen, and the mixture in the bottle was stirred at 60° C. until it was totally dissolved. The nitrogen pressure of the bottle was increased, and Pd(PPh$_3$)$_4$ (381 mg, 0.33 mmol) was rapidly added into the bottle. The reaction was heated to 110° C., and stirred for 48 hours. The resulting was filtered to remove metal. The filtrate was condensed to remove the solvent. The solid was washed by water and methanol, and then sublimated at a temperature of 260° C. to obtain TSTP (1.50 g, yield=82%) as white solid.

$^1$H NMR (400 MHz, CDCl$_3$): δ 8.80 (s, 1H), 8.72-8.63 (m, 5H), 7.84 (d, J=8.4 Hz, 1H), 7.66-7.64 (m, 4H), 7.56 (d, J=8.0 Hz, 2H), 7.18-7.04 (m, 17H).

$^{13}$C NMR (100 MHz, CDCl$_3$): δ 143.7, 143.1, 141.2, 140.5, 139.3, 138.7, 132.0, 131.4, 131.4, 130.0, 129.8, 129.8, 129.6, 128.8, 127.8, 127.7, 127.7, 127.3, 127.2, 126.5, 126.5, 126.1, 123.8. 123.3, 121.4.

HRMS (m/z): [M$^+$] calcd. for C$_{44}$H$_{30}$, 558.2348. Found, 558.2344.

Anal. calcd for C$_{44}$H$_{30}$: C, 94.59; H, 5.41. Found: C, 94.45; H, 5.39.

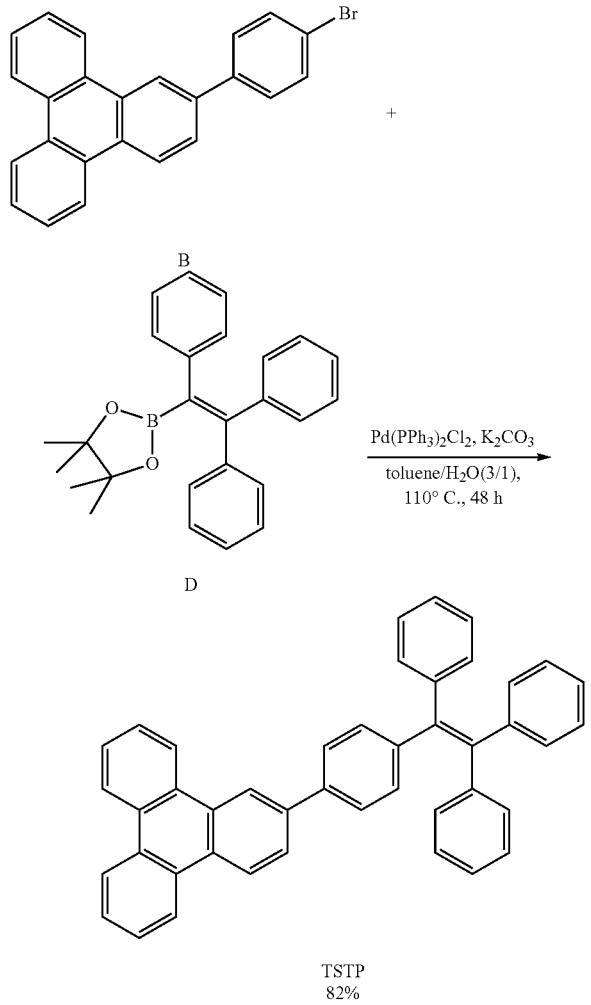

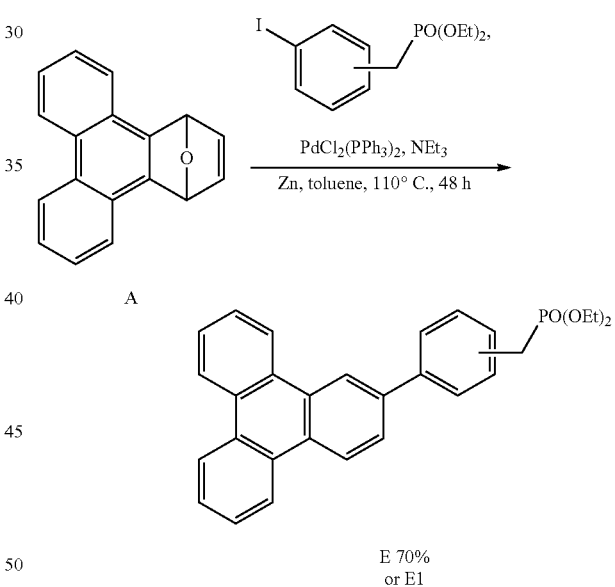

Diethyl 4-(triphenylen-2-yl)benzylphosphonate (E)

Compound A (760 mg, 3.11 mmol), zinc (1.85 g, 28.2 mmol), and PdCl$_2$(PPh$_3$)$_2$ (198 mg, 0.28 mmol) were charged in a two-necked bottle. The bottle was then vacuumed and purged with nitrogen, and dried toluene (30 mL), diethyl 4-iodobenzylphosphonate (0.65 mL, 2.82 mmol) or diethyl 3-iodobenzylphosphonate, and triethyl amine (3.91 mL, 28.2 mmol) were added to the bottle. The mixture in the bottle was heated to 110° C. for reaction for 48 hours, and the resulting was filtered to remove metal. The filtrate was condensed to remove the solvent, and then purified by column chromatography (ethyl acetate/hexanes=1/2) to obtain E (0.90 g, yield=70%) as white solid.

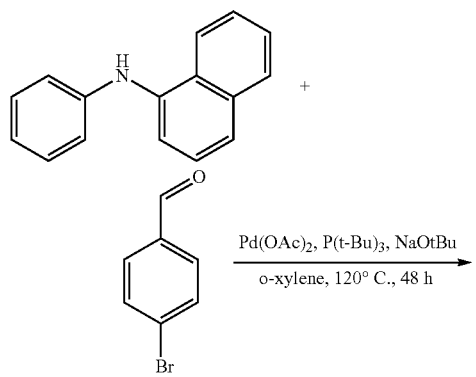

F
63%

4-(Naphthalen-1-yl(phenyl)amino)benzaldehyde (F)

4-Bromobenzaldehyde (1.00 g, 5.40 mmol), 1-anilinonaphthalene (1.42 g, 6.48 mmol) and Pd(OAc)$_2$ (25 mg, 0.11 mmol) and NaOtBu (623 mg, 6.48 mmol) were charged in a sealed tube. The sealed tube was deoxygenated and purged with nitrogen, and added dried o-xylene (30 mL) and tri-tert-butylphosphine (0.23 ml, 0.11 mmol). The reaction was heated to 120° C., and stirred for 48 hours. The resulting was filtered to remove metal and then concentrated under reduced pressure and the residue was purified by column chromatography (hexanes/CH$_2$Cl$_2$=1/1) to afford F (1.10 g, 63%) as yellow solid.

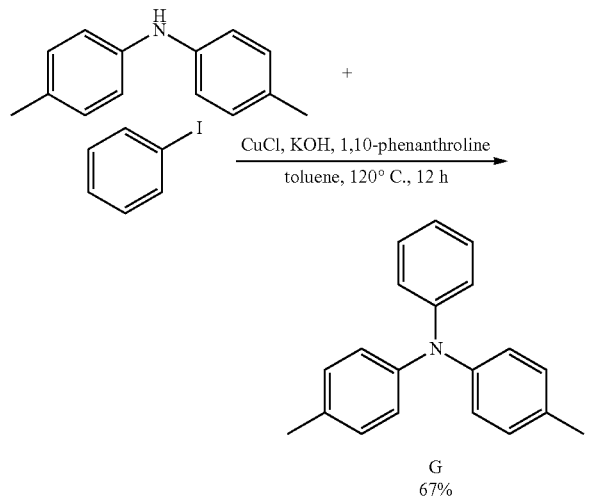

G
67%

4-Methyl-N-phenyl-N-p-tolylaniline (G)

4,4'-dimethyldiphenylamine (0.99 g, 5.0 mmol), KOH (2.52 g, 45.0 mmol), CuCl (99 mg, 1.0 mmol) and 1,10-phenanthroline (180 mg, 1.0 mmol) were charged in a two-necked bottle. The bottle was deoxygenated and purged with nitrogen, and added dried toluene (12 mL) and iodobenzene (0.67 ml, 6.0 mmol). The reaction was heated to 120° C., and stirred for 12 hours. The resulting was filtered to remove metal and then concentrated under reduced pressure and the residue was purified by column chromatography (hexanes/CH$_2$Cl$_2$=1/1) to afford G (916 g, 67%) as white solid.

$^1$H NMR (400 MHz, CDCl$_3$): δ 7.22-7.18 (m, 2H), 7.07-6.91 (m, 11H), 2.31 (s, 6H).

$^{13}$C NMR (100 MHz, CDCl$_3$): δ 148.3, 145.4, 132.3, 129.8, 129.0, 124.4, 122.9, 121.7, 20.8.

HRMS (m/z): [M$^+$] calcd. for C$_{20}$H$_{19}$N, 273.1517. Found, 273.1516.

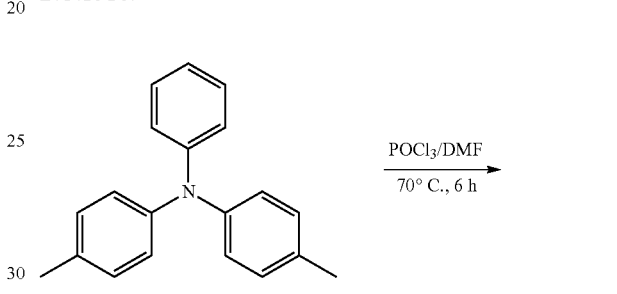

G

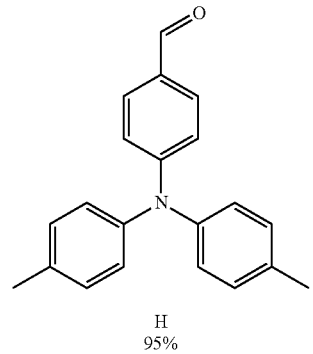

H
95%

4-(Dip-tolylamino)benzaldehyde (H)

N,N-dimethylformamide (6.0 ml) was charged in a two-necked bottle. The bottle was deoxygenated and purged with nitrogen, and added POCl$_3$ (0.86 mL, 5.27 mmole) in an ice bath, and then stirred for 30 mins. Compound G was in DMF (6.0 ml) was added stepwise. The reaction was heated to 70° C., and stirred for 6 hours. The resulting was distilled to remove solvent under reduced pressure and the residue was purified by column chromatography (hexanes/CH$_2$Cl$_2$=6/1) to afford H (1.26 g, 95%) as yellow solid.

$^1$H NMR (400 MHz, CDCl$_3$): δ 9.75 (s, 1H), 7.62 (d, J=8.8 Hz, 2H), 7.13 (d, J=8.0 Hz, 4H), 7.05 (d, J=8.0 Hz, 4H), 6.92 (d, J=8.8 Hz, 2H), 2.33 (s, 6H).

$^{13}$C NMR (100 MHz, CDCl$_3$): δ 190.4, 153.7, 143.5, 135.0, 131.3, 130.3, 128.3, 126.4, 118.2, 21.0.

HRMS (m/z): [M$^+$] calcd. for C$_{21}$H$_{19}$NO, 301.1467. Found, 301.1471.

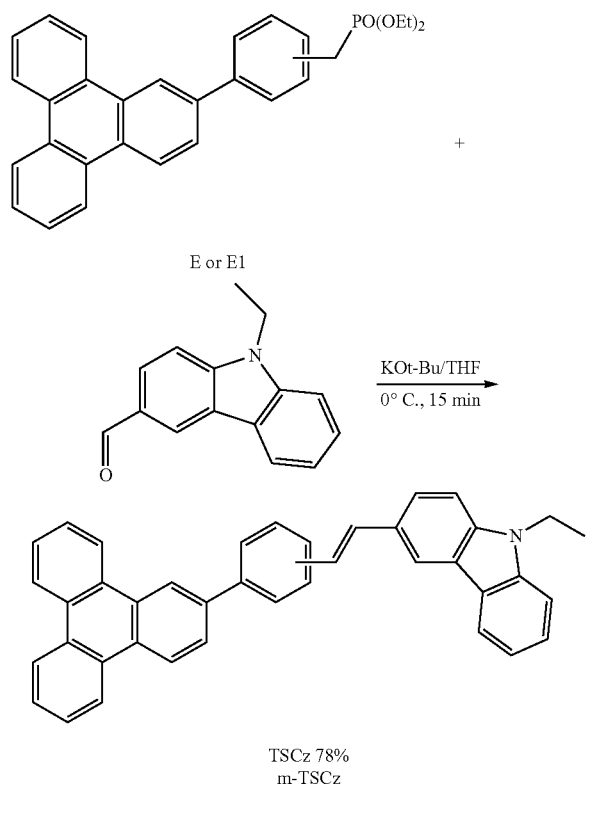

(E)-9-Ethyl-3-(4-(triphenylen-2-yl)styryl)-9H-carbazole (TSCz)

Compound E (100 mg, 0.22 mmol) or E1 and N-ethylcarbazole-3-carboxaldehyde) (59 mg, 0.26 mmol) and dry THF (10 ml) were charged in two-necked bottle in an ice bath, potassium-tert-butoxide (49 mg, 0.44 mmol) in dry THF (10 ml) was added under nitrogen. The reaction mixture was stirred for 15 min at 0° C., followed by 1 h at room temperature. The solution mixture was extracted with ethyl acetate and washed with water. The combined organic layers were dried over MgSO$_4$ and the solvent removed under reduced pressure to afford a crude product that was purified by sublimating at a temperature of 260° C. to obtain TSCz (90 mg, yield=78%) as yellow solid.

$^1$H NMR (400 MHz, CDCl$_3$): δ 8.89 (d, J=1.6 Hz, 1H), 8.78-8.65 (m, 5H), 8.28 (d, J=1.2 Hz, 1H), 8.14 (d, J=7.6 Hz, 1H), 7.94 (dd, J=8.4, J=2.0 Hz, 1H), 7.83 (d, J=8.0 Hz, 2H), 7.73-7.65 (m, 7H), 7.50-7.39 (m, 4H), 7.27-7.23 (m, 2H), 4.38 (q, J=7.2 Hz, 2H), 1.45 (t, J=7.2 Hz, 3H).

$^{13}$C NMR (100 MHz, CDCl$_3$): δ 140.2, 139.6, 139.4, 137.2, 130.0, 130.0, 129.8, 129.7, 129.7, 129.6, 128.7, 128.5, 127.5, 127.2, 127.1, 127.0, 126.7, 126.0, 125.8, 125.4, 124.5, 123.8, 123.3, 122.9, 121.3, 120.5, 119.1, 118.8, 108.5, 37.6, 13.9.

HRMS (m/z) calcd. for C$_{40}$H$_{29}$N, 523.2300. Found, 523.2299.

Anal. calcd for C$_{40}$H$_{29}$N: C, 91.74; H, 5.58; N, 2.67. Found: C, 91.37; H, 5.80; N, 2.43.

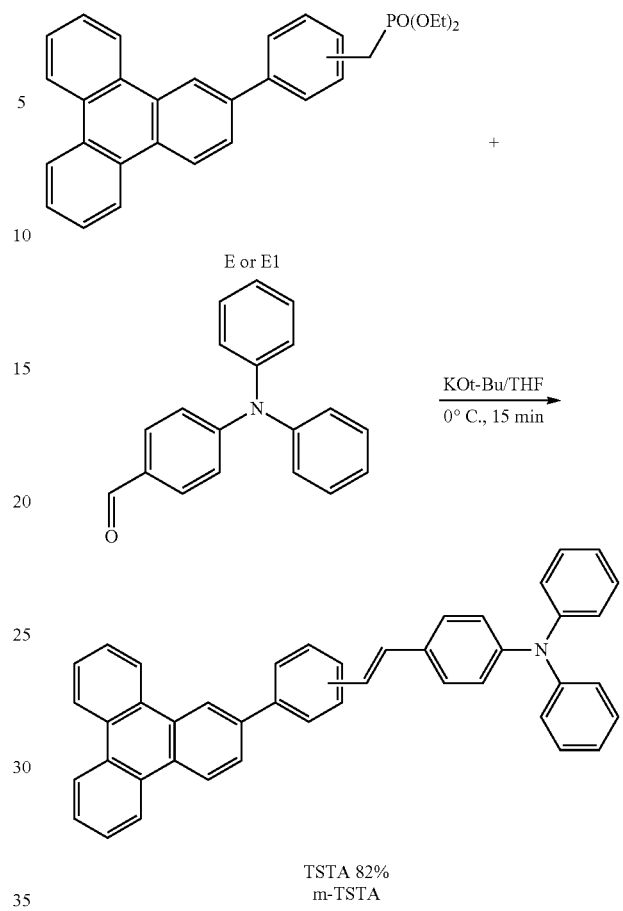

(E)-N,N-diphenyl-4-(4-(triphenylen-2-yl)styryl) aniline (TSTA)

Compound E (1.0 g, 2.20 mmol) or E1 and 4-(N,N-diphenylamino)benzaldehyde (0.72 g, 2.64 mmol) and dry THF (20 ml) were charged in two necked-bottle in an ice bath, potassium-tert-butoxide (0.49 g, 4.4 mmol) in dry THF (20 ml) was added under nitrogen. The reaction mixture was stirred for 15 min at 0° C., followed by 1 h at room temperature. The solution mixture was extracted with ethyl acetate and washed with water. The combined organic layers were dried over MgSO$_4$ and the solvent removed under reduced pressure to afford a crude product that was purified by sublimating at a temperature of 260° C. to obtain TSTA (1.04 g, yield=82%) as yellow solid.

$^1$H NMR (400 MHz, CD$_2$Cl$_2$): δ 8.93 (d, J=1.6 Hz, 1H), 8.81-8.69 (m, 5H), 7.98 (dd, J=8.4, J=1.6 Hz, 1H), 7.86 (d, J=8.0 Hz, 2H), 7.73-7.68 (m, 6H), 7.46 (d, J=8.4 Hz, 2H), 7.31-7.27 (m, 4H), 7.22-7.04 (m, 10H).

$^{13}$C NMR (100 MHz, CD$_2$Cl$_2$): δ 147.9, 140.0, 139.7, 137.5, 131.8, 130.5, 130.4, 130.1, 130.0, 129.7, 129.3, 128.8, 127.9, 127.8, 127.3, 126.7, 126.5, 125.0, 124.4, 123.8, 123.5, 121.7.

HRMS (m/z): [M$^+$] calcd. for C$_{44}$H$_{31}$N, 573.2457. Found, 573.2460.

Anal. calcd for C$_{44}$H$_{31}$N: C, 92.11; H, 5.45; N, 2.44. Found: C, 91.94; H, 5.46; N, 2.45.

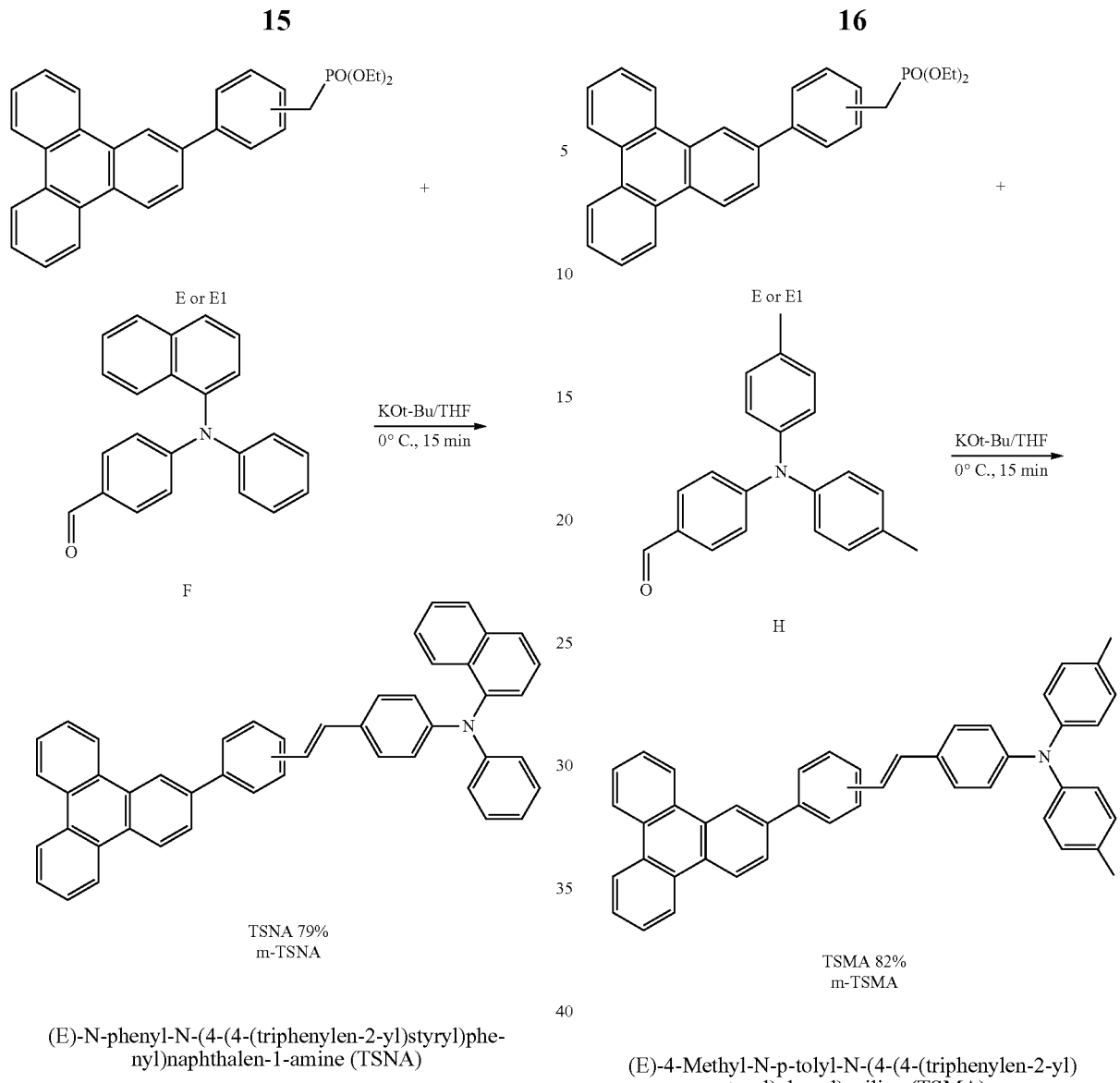

(E)-N-phenyl-N-(4-(4-(triphenylen-2-yl)styryl)phenyl)naphthalen-1-amine (TSNA)

Compound E (1.06 g, 2.23 mmol) or E1 and F (0.91 g, 2.8 mmol) and dry THF (20 ml) were charged in two-necked bottle in an ice bath; potassium-tert-butoxide (523 mg, 4.66 mmol) in dry THF (20 ml) was added under nitrogen. The reaction mixture was stirred for 15 min at 0° C., followed by 1 h at room temperature. The solution mixture was extracted with ethyl acetate and washed with water. The combined organic layers were dried over $MgSO_4$ and the solvent removed under reduced pressure to afford a crude product that was purified by sublimating at a temperature of 320° C. to obtain TSNA (1.15 g, yield=79%) as yellow solid.

$^1$H NMR (400 MHz, $CDCl_3$): δ 8.90 (s, 1H), 8.79-8.66 (m, 5H), 7.98-7.91 (m, 3H), 7.85-7.80 (m, 3H), 7.71-7.63 (m, 6H), 7.55-7.48 (m, 2H), 7.42-7.37 (m, 4H), 7.27-6.99 (m, 9H).

$^{13}$C NMR (100 MHz, $CDCl_3$): δ 148.5, 148.4, 143.6, 139.8, 139.6, 137.5, 135.8, 131.6, 130.8, 130.4, 130.4, 130.1, 129.9, 129.5, 129.2, 128.8, 128.7, 127.8, 127.7, 127.2, 127.1, 126.8, 126.6, 126.4, 126.2, 124.4, 124.3, 123.7, 122.8, 122.6, 121.6, 121.5.

HRMS (m/z): [M$^+$] calcd. for $C_{48}H_{33}N$, 623.2613. Found, 623.2616.

Anal. calcd for $C_{48}H_{33}N$: C, 92.42; H, 5.33; N, 2.25. Found: C, 92.38; H, 5.08; N, 2.33.

(E)-4-Methyl-N-p-tolyl-N-(4-(4-(triphenylen-2-yl)styryl)phenyl)aniline (TSMA)

Compound E (1.20 g, 2.64 mmol) or E1 and H (0.96 g, 3.17 mmol) and dry THF (20 ml) were charged in two-necked bottle in an ice bath, potassium-tert-butoxide (593 mg, 5.28 mmol) in dry THF (20 ml) was added under nitrogen. The reaction mixture was stirred for 15 min at 0° C., followed by 1 h at room temperature. The solution mixture was extracted with ethyl acetate and washed with water. The combined organic layers were dried over $MgSO_4$ and the solvent removed under reduced pressure to afford a crude product that was purified by sublimating at a temperature of 290° C. to obtain TSMA (1.15 g, yield=82%) as yellow solid.

$^1$H NMR (400 MHz, $CD_2Cl_2$): δ 8.92 (d, J=1.2 Hz, 1H), 8.81-8.69 (m, 5H), 7.97 (d, J=8.4, J=1.6 Hz, 1H), 7.85 (d, J=8.4 Hz, 2H), 7.73-7.66 (m, 6H), 7.41 (d, J=8.8 Hz, 2H), 7.20-6.97 (m, 12H), 2.33 (s, 6H).

$^{13}$C NMR (100 MHz, $CD_2Cl_2$): δ 148.4, 145.4, 139.8, 139.7, 137.5, 133.4, 130.7, 130.4, 130.4, 130.3, 130.1, 129.9, 129.2, 128.9, 127.8, 127.8, 127.7, 127.6, 127.2, 126.4, 126.1, 125.2, 124.3, 123.7, 122.4, 121.7, 20.9.

HRMS (m/z): [M$^+$] calcd. for $C_{46}H_{35}N$, 601.2770. Found, 601.2767.

Anal. calcd for $C_{46}H_{35}N$: C, 91.81; H, 5.86; N, 2.33. Found: C, 91.67; H, 5.92; N, 2.32.

Luminescence Properties of Triphenylene Derivatives

Referring to table 1, the emitting length for triphenylene derivatives ranges from 384 to 462 nm and matches blue light. The FWHM thereof ranges from 50-59 nm.

TABLE 1

Luminescence properties of triphenylene derivatives

| Compound | $\lambda_{abs}$ in toluene (nm) | $\lambda_{em}$ in toluene (nm) | $\lambda_{abs}$ in (thin fim) (nm) | $\lambda_{em}$ in (thin film) (nm) | FWHM in toluene (nm) | Q.Y. |
|---|---|---|---|---|---|---|
| TSP | 260, 292, 337 | 384, 404 | 301, 338 | 451 | 50 | — |
| TSDP | 258, 290, 350 | 384, 404 | 301, 350 | 451 | 53 | — |
| TSTP | 258, 274, 328 | N.D. | 258, 279, 344 | 484 | N.D. | N.D. |
| TSCz | 358 | 420, 442 | 359 | 469 | 55 | 85 |
| TSTA | 308, 386 | 441, 462 | 315, 390 | 470 | 56 | 87 |
| TSNA | 386 | 441, 462 | 311, 395 | 469 | 56 | >90 |
| TSMA | 308, 392 | 451 | 315, 402 | 470 | 59 | >90 |

N.D.: Non-detected

OLED Configuration

Refer to FIGURE, which is a schematic diagram illustrating an organic light emitting device containing triphenylene derivatives according to one embodiment of the present invention. The light emitting device includes an emitting layer 3 configured between an anode 1 and a cathode 2. The emitting layer 3 includes host emitting material doped with light emitting material. The light emitting device may also include a hole injecting layer 7, a hole transport layer 4, an electron blocking layer 9, an emitting layer 3, a hole blocking layer 6, an electron transport layer 5 and an electron injecting layer 8 sequentially configured on top of the anode 1. The real thickness of each layer doesn't correspond to the schematic size, and the above-mentioned electron blocking layer 9, hole blocking layer 6 and electron injecting layer 8 may be optional.

The triphenylene derivatives of the present invention may be used as a host emitter or a dopant in the light emitting layer.

Configuration of Doped OLED

A device structure of a doped OLED is herein illustrated, where ITO is used for a substrate and an electrode; the tested electrode includes LiF/Al; the host emitting layer contains DMPPP as the host emitter doped with 5% example compounds of the present invention; the tested hole transport layer includes TCTA (4,4',4"-tri(N-carbazolyl)triphenylamine); and the tested electron transport layer includes BCP (2,9-dimethyl-4,7-diphenyl-[1,10]phenanthroline). In addition, a control group includes BCzVBi (4,4'-(Bis(9-ethyl-3-carbazovinylene)-1,1'-biphenyl) as the reference dopant.

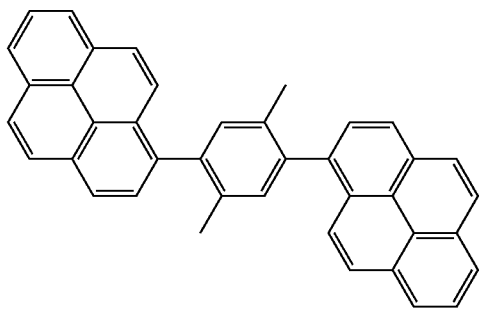

DMPPP

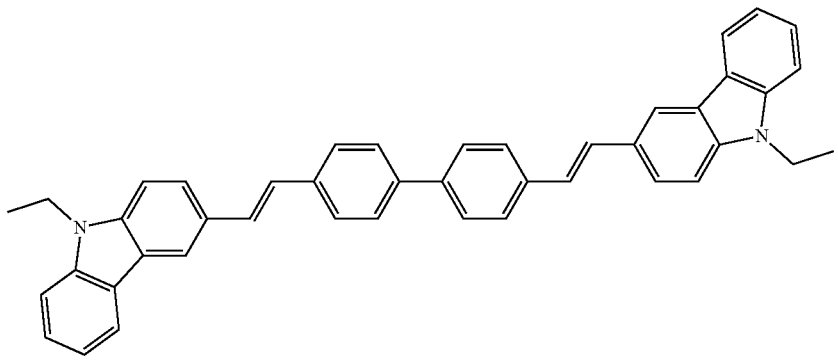

BCzVBi

The detailed configuration and width (nm) of the tested devices are respectively illustrated as followings, and the measured performance is listed in Table 2.

Device A: TCTA(50)/DMPPP:TSCz(5%)(40)/BCP(30)/LiF(1)/Al(100)
Device B: TCTA(50)/DMPPP:TSTA(5%)(40)/BCP(30)/LiF(1)/Al(100)
Device C: TCTA(50)/DMPPP:TSNA(5%)(40)/BCP(30)/LiF(1)/Al(100)
Device D: TCTA(50)/DMPPP:TSMA(5%)(40)/BCP(30)/LiF(1)/Al(100)
Device E: TCTA(50)/DMPPP:BCzVBi(5%)(40)/BCP(30)/LiF(1)/Al(100)

TABLE 2

Performance of doped OLEDs containing the triphenylene derivatives of the present invention

| Device | Dopant (5%) | E.Q.E. (%) (V) | C.E. (cd/A) | P.E. (lm/W) | Max. Brightness (cd/m$^2$) (V) | $V_d$ (V) | EL $\lambda_{max}$ (nm) | FWHM (nm) | CIE (x, y) | Life hours ($T_{50}$@ 2000 nit, h) |
|---|---|---|---|---|---|---|---|---|---|---|
| A | TSCz | 6.5 (6.5) | 5.1 | 2.8 | 18420 (14.5) | 3.1 | 436 | 57 | (0.15, 0.08) | — |
| B | TSTA | 9.0 (10.0) | 9.9 | 4.8 | 53252 (18.0) | 3.3 | 454 | 57 | (0.14, 0.12) | 211 |
| C | TSNA | 9.2 (10.0) | 9.2 | 5.1 | 45490 (18.5) | 3.7 | 450 | 55 | (0.15, 0.11) | 252 |
| D | TSMA | 9.4 (9.5) | 11.1 | 5.9 | 54579 (18.0) | 3.5 | 458 | 58 | (0.14, 0.14) | 230 |
| E | BCzVBi | 7.7 (8.5) | 8.3 | 3.9 | 41437 (18.0) | 3.2 | 450 | 53 | (0.14, 0.12) | 167 |

Here, the devices B, C and D that are respectively doped with TSTA, TSNA and TSMA have achieved better lighting performance in C.E., P.E., max brightness, FWHM, CIE(x,y) and life hours.

To sum up, the triphenylene derivatives of the present invention may emit blue light and function as a host emitter or a dopant to be used in an organic light emitting device with advantages such as higher efficiency, lower operating voltage, higher brightness and higher life hours for devices.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A triphenylene derivative having a structure of formula (5):

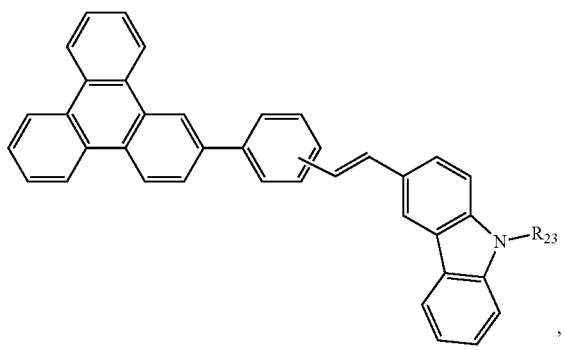

(5)

wherein $R_{23}$ is a member selected from the group consisting of hydrogen, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, substituted or unsubstituted aryl and substituted or unsubstituted heteroaryl.

2. The triphenylene derivative as claimed in claim 1, being a member selected from the group consisting of TSCz ((E)-9-Ethyl-3-(4-(triphenylen-2-yl)styryl)-9H-carbazole).

3. An organic light emitting diode, comprising:
a cathode;
an anode; and
an emitting layer configured between the cathode and the anode and comprising a triphenylene derivative having a structure of formula (5):

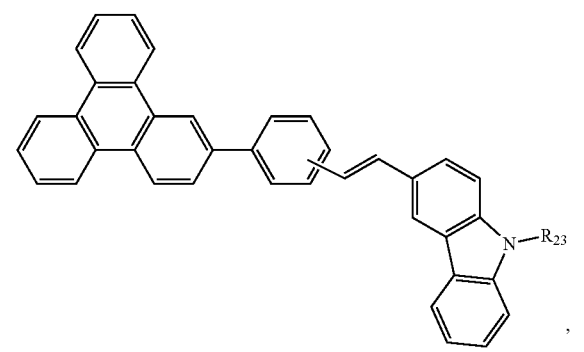

(5)

wherein $R_{23}$ is a member selected from the group consisting of hydrogen, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, substituted or unsubstituted aryl and substituted or unsubstituted heteroaryl.

4. The organic light emitting diode as claimed in claim 3, wherein the triphenylene derivative is a member selected from the group consisting of TSCz ((E)-9-Ethyl-3-(4-(triphenylen-2-yl)styryl)-9H-carbazole).

5. The organic light emitting diode as claimed in claim 3, wherein the triphenylene derivative is a host emitter.

6. The organic light emitting diode as claimed in claim 3, wherein the triphenylene derivative is a dopant.

7. The organic light emitting diode as claimed in claim 3, wherein the organic light emitting diode is a blue organic light emitting diode.

* * * * *